United States Patent
Kim et al.

(10) Patent No.: US 9,934,939 B2
(45) Date of Patent: Apr. 3, 2018

(54) SCANNING ELECTRON MICROSCOPE SYSTEM CAPABLE OF MEASURING IN-CELL OVERLAY OFFSET USING HIGH-ENERGY ELECTRON BEAM AND METHOD THEREOF

(71) Applicant: Samsung Electronics Co., Ltd., Suwon-si, Gyeonggi-do (KR)

(72) Inventors: Min Kook Kim, Goyang-si (KR); Woo Seok Ko, Seoul (KR); Yu Sin Yang, Seoul (KR); Sang Kil Lee, Yongin-si (KR); Chung Sam Jun, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 57 days.

(21) Appl. No.: 14/464,325

(22) Filed: Aug. 20, 2014

(65) Prior Publication Data

US 2015/0115154 A1 Apr. 30, 2015

(30) Foreign Application Priority Data

Oct. 29, 2013 (KR) .......................... 10-2013-0129556

(51) Int. Cl.
*H01J 37/28* (2006.01)
*H01J 37/22* (2006.01)
(Continued)

(52) U.S. Cl.
CPC .............. *H01J 37/28* (2013.01); *G01N 23/22* (2013.01); *G03F 7/70633* (2013.01);
(Continued)

(58) Field of Classification Search
CPC ....... H01J 2237/063; H01J 2237/24475; H01J 2237/2448; H01J 2237/2806;
(Continued)

(56) References Cited

U.S. PATENT DOCUMENTS

| | | | |
|---|---|---|---|
| 4,149,085 A | 4/1979 | Davis et al. | |
| 5,607,801 A | 3/1997 | Nozue | |

(Continued)

FOREIGN PATENT DOCUMENTS

| | | |
|---|---|---|
| JP | 11-260306 | 9/1999 |
| JP | 2011-174858 | 9/2011 |
| KR | 1020010080558 A | 8/2001 |

OTHER PUBLICATIONS

Kim, Hyung-Seop et al., "Study of the Critical Dimension Shrinkage Caused by After Development Inspection," Journal of the Korean Physical Society, vol. 59, No. 2, Aug. 2011, pp. 461-465.
(Continued)

*Primary Examiner* — Wyatt Stoffa
*Assistant Examiner* — Hsien Tsai
(74) *Attorney, Agent, or Firm* — Myers Bigel, P.A.

(57) ABSTRACT

A method of measuring an overlay offset using a scanning electron microscope system includes: scanning an in-cell region, which includes a lower structure and an upper structure stacked in a sample, using a primary electron beam with a landing energy of at least 10 kV; detecting electrons emitted from the scanned in-cell region; and measuring an overlay offset with respect to overlapping patterns included in the in-cell region using an image of the in-cell region that is generated based on the detected electrons emitted from the scanned in-cell region.

13 Claims, 9 Drawing Sheets

(51) Int. Cl.
*G01N 23/22* (2018.01)
*G03F 7/20* (2006.01)
*G01N 23/203* (2006.01)
*G01N 23/225* (2018.01)

(52) U.S. Cl.
CPC .......... *H01J 37/222* (2013.01); *G01N 23/203* (2013.01); *G01N 23/2206* (2013.01); *G01N 23/2251* (2013.01); *H01J 2237/063* (2013.01); *H01J 2237/2448* (2013.01); *H01J 2237/24475* (2013.01); *H01J 2237/2806* (2013.01); *H01J 2237/2814* (2013.01)

(58) Field of Classification Search
CPC .. H01J 2237/2814; H01J 37/222; H01J 37/28; G01N 23/203; G01N 23/22; G01N 23/2206; G01N 23/2251
USPC .................................................. 250/307, 310
See application file for complete search history.

(56) References Cited

U.S. PATENT DOCUMENTS

| | | | |
|---|---|---|---|
| 5,608,218 A | 3/1997 | Sato et al. | |
| 6,366,688 B1* | 4/2002 | Jun | G01R 31/2886 250/311 |
| 6,376,136 B1 | 4/2002 | Nakasugi et al. | |
| 6,646,262 B1 | 11/2003 | Todokoro et al. | |
| 8,058,614 B2 | 11/2011 | Bihr et al. | |
| 2006/0284081 A1* | 12/2006 | Miyamoto | H01J 37/28 250/307 |
| 2008/0254637 A1* | 10/2008 | Hanson | H01L 21/0273 438/711 |
| 2009/0321634 A1* | 12/2009 | Khursheed | H01J 37/05 250/307 |
| 2012/0019648 A1 | 1/2012 | Hoshino et al. | |
| 2012/0211654 A1 | 8/2012 | Iwaya et al. | |
| 2012/0292502 A1* | 11/2012 | Langer | G01N 23/2251 250/307 |
| 2013/0026361 A1* | 1/2013 | Yamanashi | H01J 37/1478 250/307 |
| 2013/0277554 A1* | 10/2013 | Ren | H01J 37/261 250/310 |

OTHER PUBLICATIONS

Joy, David C., "Overview of CD-SEM—and beyond," CP683, Characterization and Metrology for ULSI Technology, 2003 International Conference, pp. 619-626.

\* cited by examiner

SCANNING ELECTRON MICROSCOPE SYSTEM CAPABLE OF MEASURING IN-CELL OVERLAY OFFSET USING HIGH-ENERGY ELECTRON BEAM AND METHOD THEREOF

CROSS-REFERENCE TO RELATED APPLICATIONS

This application claims priority under 35 U.S.C. § 119(a) from Korean Patent Application No. 10-2013-0129556, filed on Oct. 29, 2013, the disclosure of which is hereby incorporated by reference in its entirety.

FIELD

Embodiments of the inventive concept relate to a scanning electron microscope (SEM) system, and more particularly, to a SEM system capable of measuring an in-cell overlay offset using a high-energy electron beam and a method thereof.

BACKGROUND

A SEM system scans a sample using a focused electron beam to observe the surface state of the sample or analyze the components of the sample using a signal based on or related to secondary electrons or back-scattered electrons emitted from the sample.

An overlay offset does not represent an actual circuit pattern due to a physical distance between the actual circuit pattern and an optical overlay measurement pattern (e.g., an alignment mark) implemented within a scribe line of a wafer. In manufacturing a wafer, process steps are ideally perfectly aligned with one another. A photo scanner performs alignment using an overlay measurement result. When there is misalignment between two process steps, an overlay offset occurs. The overlay offset is compensated for through a compensation process.

SUMMARY

According to some embodiments of the inventive concept, there is provided a method of measuring an overlay offset using a scanning electron microscope (SEM) system. The method includes scanning an in-cell region, which includes a lower structure and an upper structure stacked in a sample, using a primary electron beam with a landing energy of at least 10 kV; detecting electrons emitted from the scanned in-cell region; and measuring an overlay offset with respect to overlapping patterns included in the in-cell region using an image of the in-cell region that is generated based on the detected electrons emitted from the scanned in-cell region.

The detected electrons may be back-scattered electrons. Alternatively, the detected electrons may be back-scattered electrons and secondary electrons.

The measuring the overlay offset may include measuring the overlay offset using the image that is generated based on the back-scattered electrons more or in a greater degree than the secondary electrons.

The in-cell region may not include alignment marks included in scribe lines. The in-cell region may be separated from scribe lines of the sample and may not include alignment marks. The in-cell region may be at an after clean inspection (ACI) step.

The measuring step may be carried out using an image processing and overlay offset measurement device.

The method may include displaying the measured overlay offset using a display.

A non-transitory computer readable recording medium storing a computer program may be configured to execute the method of measuring an overlay offset using a scanning electron microscope (SEM) system.

According to other embodiments of the inventive concept, there is provided a method of measuring an overlay offset using a SEM system. The method includes scanning an in-cell region of a sample using a primary electron beam. The in-cell region includes a lower structure and an upper structure stacked in the sample. The method further includes: detecting back-scattered electrons emitted from the scanned in-cell region; generating an image of the in-cell region that is based on the detected back-scattered electrons; and measuring an overlay offset with respect to overlapping patterns included in the in-cell region using the generated image.

The primary electron beam for the in-cell region may have a landing energy of at least 10 kV.

The method may include detecting secondary electrons emitted from the scanned in-cell region. The generated image may be based on the detected back-scattered electrons and the detected secondary electrons.

The image may be based on the back-scattered electrons to a greater degree than the secondary electrons.

The method may include displaying at least one of the generated image and the measured overlay offset.

The detecting step may be carried out using at least one detector that is positioned so as to not affect a path of the primary electron beam to the sample.

According to further embodiments of the inventive concept, there is provided a SEM system including an electron gun configured to scan an in-cell region, which includes a lower structure and an upper structure stacked in a sample, using a primary electron beam; a stage configured to support the sample; at least one first detector configured to detect back-scattered electrons emitted from the in-cell region; an image processing and overlay offset measurement device configured to generate an image of the in-cell region using the back-scattered electrons and to measure an overlay offset with respect to overlapping patterns included in the in-cell region using the image; and a voltage controller configured to control an accelerating voltage applied to the electron gun and a voltage applied to the sample so that a landing energy of the primary electron beam for the in-cell region is at least 10 kV.

The SEM system may further include at least one second detector configured to detect secondary electrons emitted from the in-cell region. At this time, the image processing and overlay offset measurement device may be configured to generate the image using the back-scattered electrons and the secondary electrons and to measure the overlay offset using the image.

The image processing and overlay offset measurement device may be configured to generate the image using the back-scattered electrons more or to a greater degree than the secondary electrons.

The SEM system may further include a display configured to display at least one of the generated image and the measured overlay offset.

BRIEF DESCRIPTION OF THE DRAWINGS

The above and other features and advantages of the inventive concept will become more apparent by describing in detail exemplary embodiments thereof with reference to the attached drawings in which:

FIGS. 6A through 8C are schematic diagrams representing images measured using a conventional SEM system and images measured using a high-energy SEM system.

DETAILED DESCRIPTION OF THE EMBODIMENTS

The inventive concept now will be described more fully hereinafter with reference to the accompanying drawings, in which embodiments of the inventive concept are shown. This inventive concept may, however, be embodied in many different forms and should not be construed as limited to the embodiments set forth herein. Rather, these embodiments are provided so that this disclosure will be thorough and complete, and will fully convey the scope of the inventive concept to those skilled in the art. In the drawings, the size and relative sizes of layers and regions may be exaggerated for clarity. Like numbers refer to like elements throughout.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. As used herein, the term "and/or" includes any and all combinations of one or more of the associated listed items and may be abbreviated as "/".

It will be understood that, although the terms first, second, etc. may be used herein to describe various elements, these elements should not be limited by these terms. These terms are only used to distinguish one element from another. For example, a first signal could be termed a second signal, and, similarly, a second signal could be termed a first signal without departing from the teachings of the disclosure.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

Figure 1:
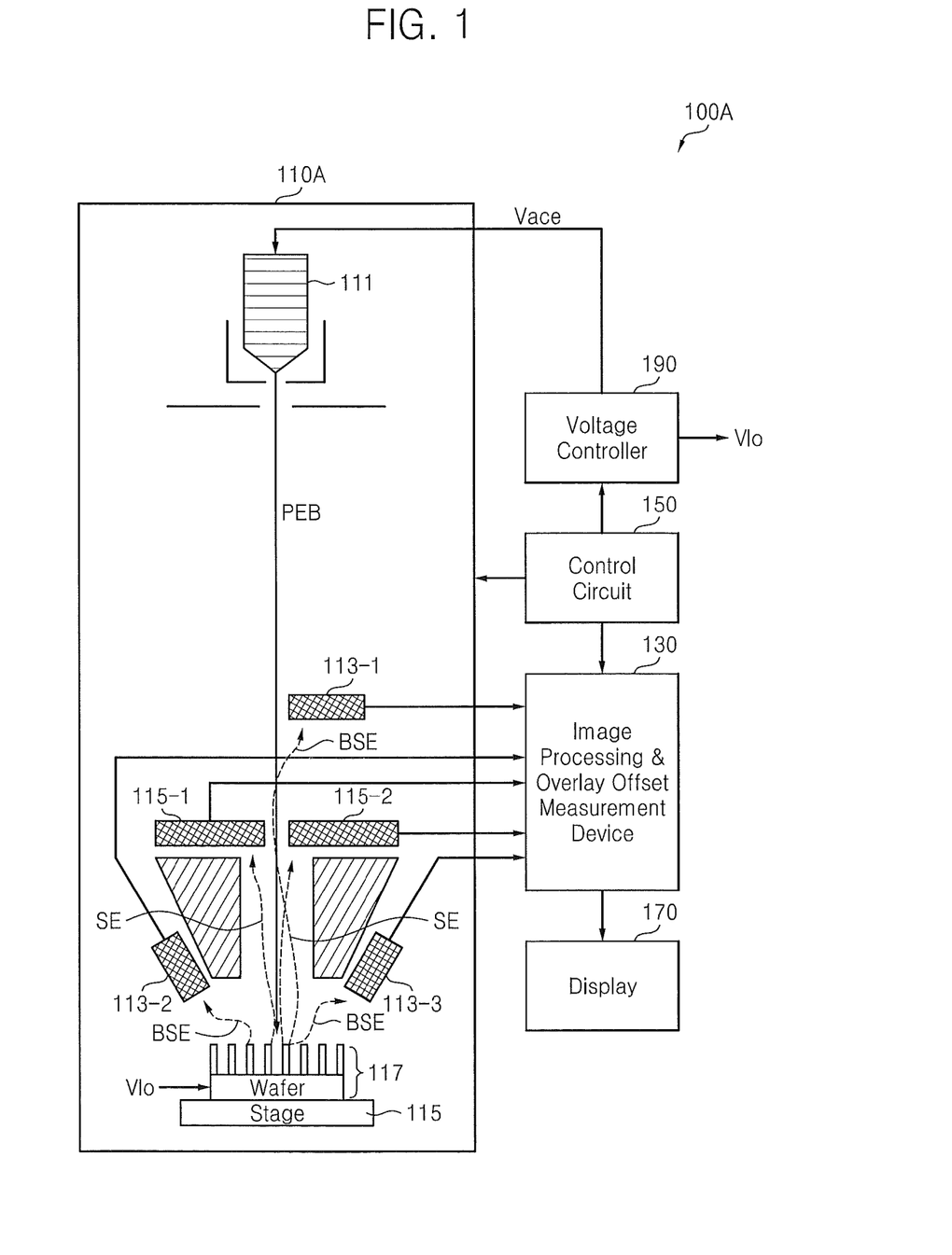
FIG. 1 is a block diagram of a scanning electron microscope (SEM) system according to some embodiments of the inventive concept.

FIG. 1 is a block diagram of a scanning electron microscope (SEM) system 100A according to some embodiments of the inventive concept. The SEM system (or the SEM) 100A includes a sample chamber 110A, an image processing and overlay offset measurement device 130, a control circuit 150, a display 170, and a voltage controller 190.

The sample chamber 110A includes an electron source 111; one or more first detectors 113-1, 113-2, and 113-3; one or more second detectors 115-1 and 115-2; a stage 115; and a sample 117. The sample chamber 110A may maintain a vacuum state, so that the stage 115 and the sample 117 are not influenced by particles.

The electron source 111, for example, a high-energy electron gun, may be implemented at an upper portion of the sample chamber 110A. The electron source 111 scans an in-cell region of the sample 117 using a primary electron beam (PEB) generated using an accelerating voltage Vace. The in-cell region will be described in detail with reference to FIG. 3 below.

One or more first detectors 113-1, 113-2, and 113-3 may detect back-scattered electrons (BSE) emitted from the in-cell region of the sample 117 based on the PEB emitted from the electron source 111 and may transmit a BSE signal corresponding to the detection result to the image processing and overlay offset measurement device 130.

One or more second detectors 115-1 and 115-2 may detect secondary electrons (SE) emitted from the in-cell region of the sample 117 based on the PEB emitted from the electron source 111 and may transmit an SE signal corresponding to the detection result to the image processing and overlay offset measurement device 130.

The detectors 113-1, 113-2, 113-3, 115-1, and 115-2 are positioned in the sample chamber 110A so as to not affect a PEB path through which the PEB emitted from the electron source 111 approaches and/or reaches the sample 117. In addition, a transmission line for transmitting the BSE or SE signal output from each of the detectors 113-1, 113-2, 113-3, 115-1, and 115-2 is positioned so as to not affect the PEB path.

The sample 117 is placed on the stage 115. The sample 117 may be a semiconductor chip or a wafer, for example. A voltage Vlo output from the voltage controller 190 is applied to the sample 117.

The voltages Vace and Vlo may be determined by the voltage controller 190 so that the in-cell region of the sample 117 has a landing energy of at least 10 kV. For instance, when the accelerating voltage Vace is 15 kV and the voltage Vlo applied to the sample 117 is −5 kV, the landing energy of the electron source 111 supplied to the sample 117 is 10 kV.

In some embodiments, the image processing and overlay offset measurement device 130 may generate an image of the in-cell region of the sample 117 using only BSE signal output from each of the first detectors 113-1, 113-2, and 113-3 and may measure an overlay offset with respect to overlapping patterns in the in-cell region using the image. In other embodiments, the image processing and overlay offset measurement device 130 may generate an image of the in-cell region of the sample 117 using the BSE signal output from each of the first detectors 113-1, 113-2, and 113-3 and the SE signal output from each of the second detectors 115-1 and 115-2 and may measure an overlay offset with respect to overlapping patterns in the in-cell region using the image.

When the image processing and overlay offset measurement device 130 generates an image of the in-cell region of the sample 117 by mixing a BSE signal with an SE signal, it may use the BSE signal related to the BSE as a dominant signal. In other words, the image processing and overlay offset measurement device 130 may generate the image of the in-cell region using more BSE (or BSE signal) than SE (or SE signal). The ratio between the SE (or the SE signal) and the BSE (or the BSE signal) may be adjusted by the control circuit 150.

The control circuit 150 may control the operations of the image processing and overlay offset measurement device 130 and the voltage controller 190. For instance, the control circuit 150 may function as a central processing unit (CPU) or a processor. In addition, the control circuit 150 may control a transport unit that controls the movement of the stage 115. Accordingly, the in-cell region of the sample 117 placed on the stage 115 may be aligned with the PEB path.

The display 170 may display the image of the in-cell region that has been processed by the image processing and overlay offset measurement device 130 or an overlay offset that has been measured by the image processing and overlay offset measurement device 130.

The voltage controller 190 may control the voltages Vace and Vlo according to the control of the control circuit 150. Accordingly, the landing energy for the in-cell region of the sample 117 may be controlled by the voltage controller 190 to be at least 10 kV.

Figure 2:
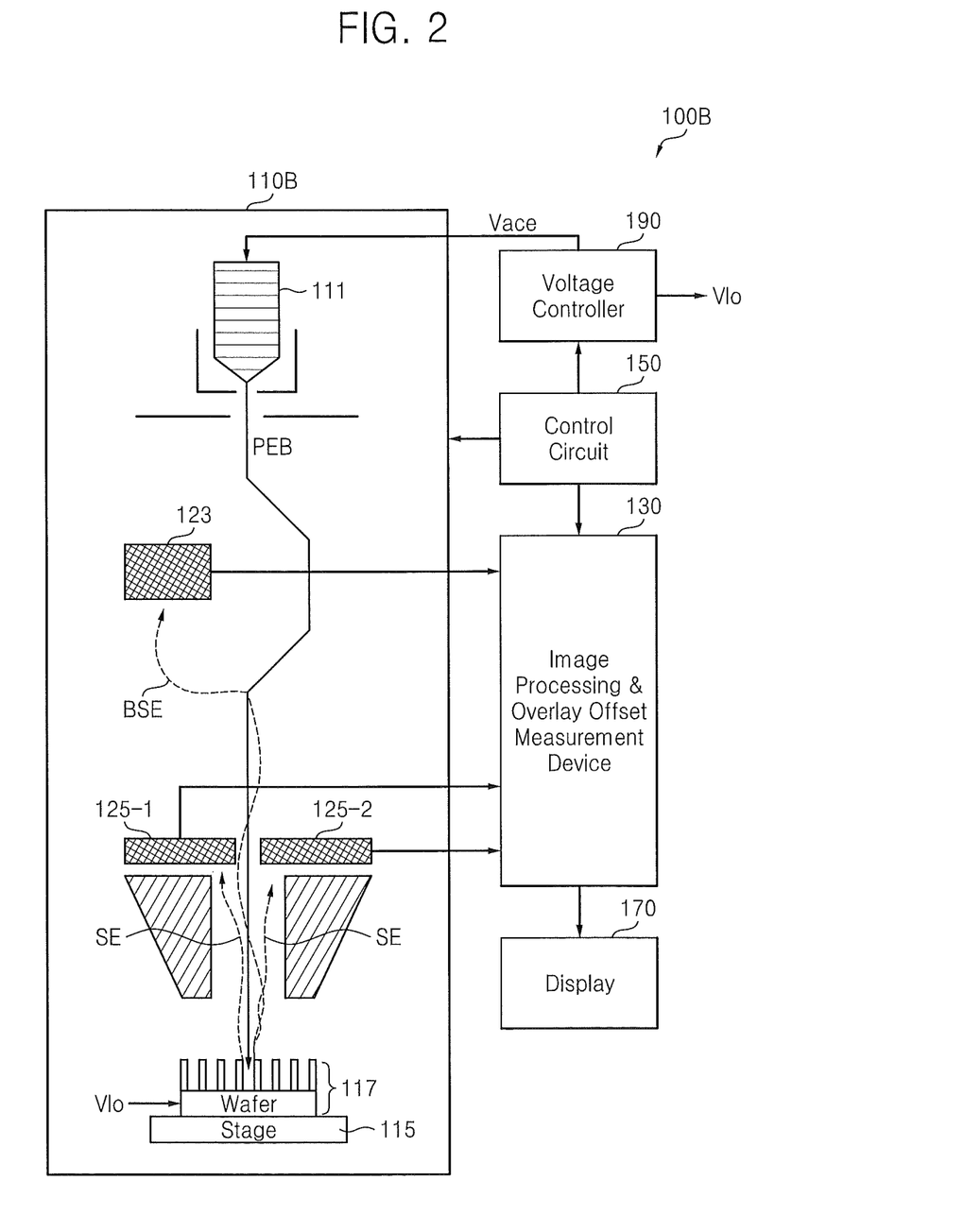
FIG. 2 is a block diagram of a SEM system according to other embodiments of the inventive concept.

FIG. 2 is a block diagram of a SEM system 100B according to other embodiments of the inventive concept. The SEM system 100B includes a sample chamber 110B, the image processing and overlay offset measurement device 130, the control circuit 150, the display 170, and the voltage controller 190.

At least one first detector 123 may detect BSE emitted from the in-cell region of the sample 117 based on a PEB emitted from the electron source 111 and may transmit a BSE signal corresponding to the detection result to the image processing and overlay offset measurement device 130. One or more second detectors 125-1 and 125-2 may detect SE emitted from the in-cell region of the sample 117 based on the PEB emitted from the electron source 111 and may transmit an SE signal corresponding to the detection result to the image processing and overlay offset measurement device 130. The operations of the elements 130, 150, 170, and 190 illustrated in FIG. 2 are substantially the same as those of the elements 130, 150, 170, and 190 illustrated in FIG. 1.

Figure 3:
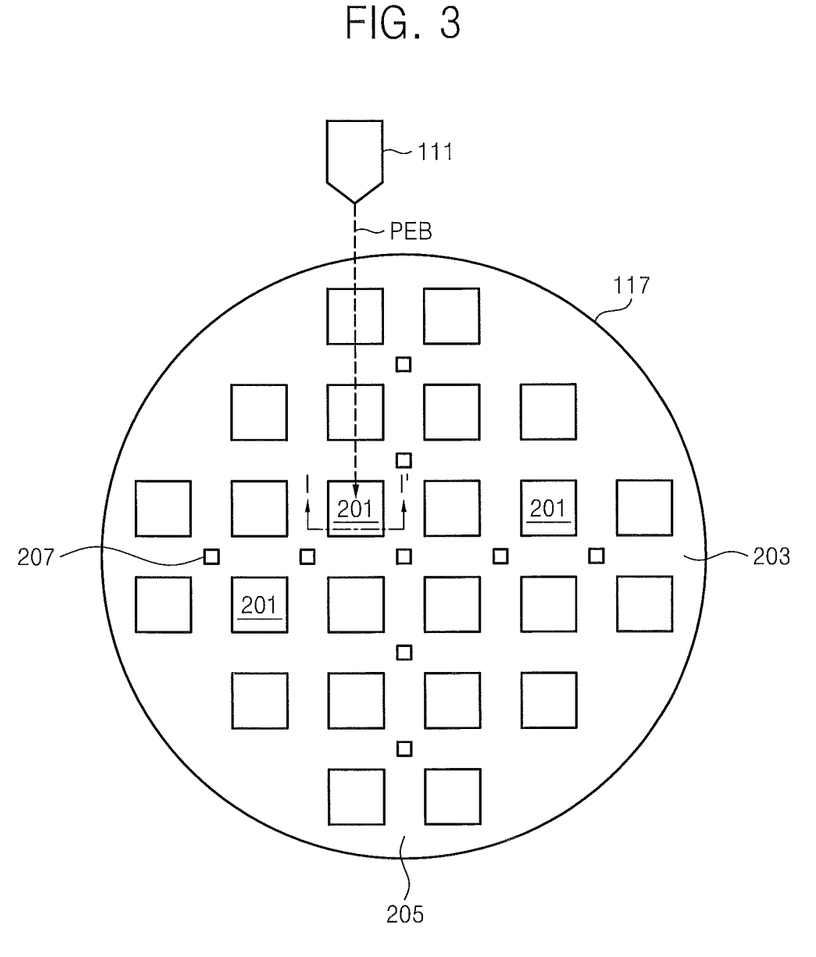
FIG. 3 is a plan view of a sample illustrated in FIGS. 1 and 2.

FIG. 3 is a plan view of the sample 117 illustrated in FIGS. 1 and 2. Referring to FIGS. 1 through 3, the sample 117 may be a wafer including a plurality of integrated circuits (IC) or chips 201. The wafer 117 includes a plurality of ICs 201, a plurality of horizontal scribe lines 203, a plurality of vertical scribe lines 205, and a plurality of alignment marks 207.

The in-cell region is an IC or a chip 201. The in-cell region is a region in which actual electronic components or actual patterns are implemented. Accordingly, the in-cell region is a region that is separated from the scribe lines 203 and 205 and does not include the alignment marks 207. The electron source 111 may scan each in-cell region 201 of the sample 117 using a PEB (e.g., emitted from the electron source 111).

Figure 4A:
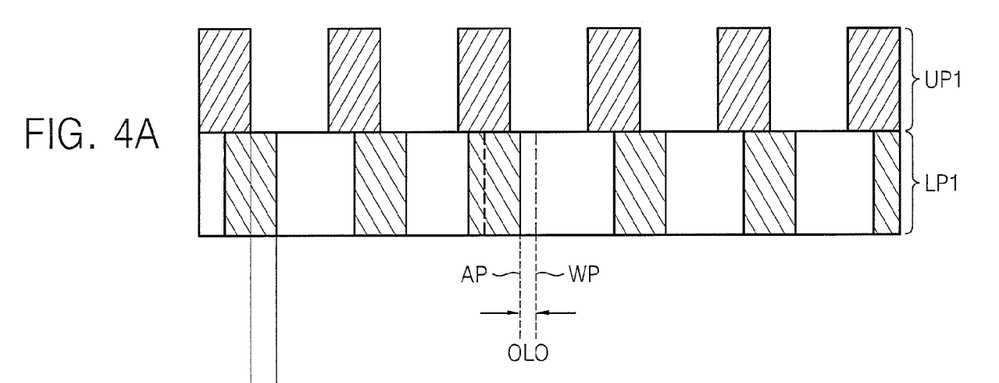
FIGS. 4A and 4B are cross-sectional views of the sample, which is illustrated in FIG. 3 and has a stack structure, taken along the I-I' direction illustrated in FIG. 3.
Figure 4B:
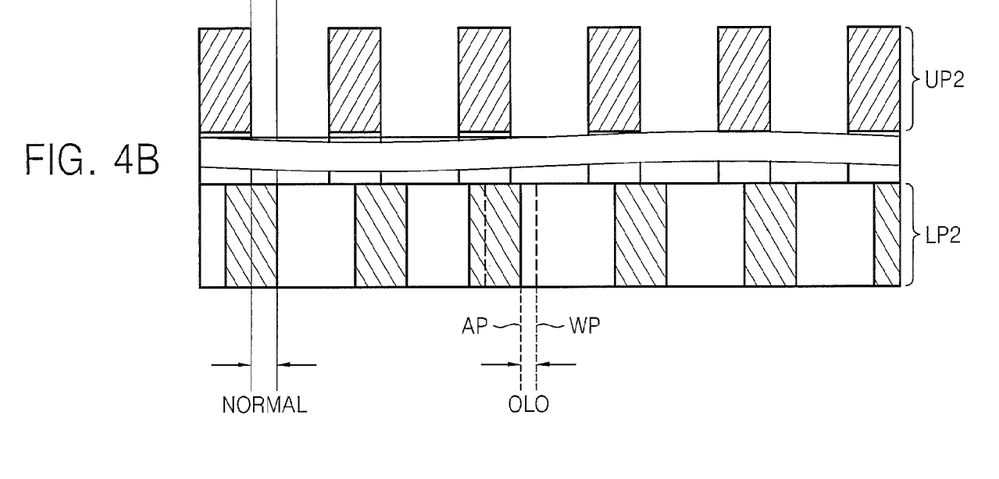

FIGS. 4A and 4B are cross-sectional views of the sample 117, which is illustrated in FIG. 3 and has a stack structure, taken along the I-I' direction illustrated in FIG. 3. Referring to FIGS. 1 through 4A, the sample 117 having the stack structure includes a lower structure LP1 and an upper structure UP1 stacked on or above the lower structure LP1.

The lower structure LP1 includes circuit patterns formed in a previous process step. The upper structure UP1 includes circuit patterns formed in a current or subsequent process step.

Referring to FIGS. 1 through 4B, the sample 117 having the stack structure includes a lower structure LP2 formed at a child step (e.g., an initial step) in a multi-step process and an upper structure UP2 formed at a mother step (e.g., a subsequent step) in the multi-step process. Each of the structures LP2 and UP2 includes circuit patterns. The samples 117 that are respectively illustrated in FIGS. 4A and 4B may be at an after clean inspection (ACI) step (e.g., the samples 117 may be provided directly after or directly before an ACI step is carried out in a multi-step process).

As shown in FIGS. 4A and 4B, a particular pattern of the lower structures LP1 and LP2 is implemented at a desired position (or designed position) in a normal state. However, an overlay offset OLO indicates a difference between a position WP at which the particular pattern of the lower structures LP1 and LP2 is supposed to be implemented (e.g., the desired position) and an actual position AP at which the particular pattern is actually implemented.

The image processing and overlay offset measurement device 130 may simultaneously generate images of the respective structures LP1 and UP1 or LP2 and UP2 included in the in-cell region based on electrons emitted from the in-cell region in response to a PEB radiated at the in-cell region of the sample 117 and may measure the overlay offset OLO with respect to overlapping circuit patterns (i.e., overlaid circuit patterns in the stacked structures LP1 and UP1 or LP2 and UP2) included in the in-cell region using the images.

As described above, the image processing and overlay offset measurement device 130 may generate an image of an in-cell region using only a BSE signal related to or based on BSE only or may generate an image of an in-cell region by mixing a BSE signal related to or based on BSE with an SE signal related to or based on SE. When generating the image of the in-cell region by mixing the BSE signal with the SE signal, the image processing and overlay offset measurement device 130 may generate the image using the BSE signal as a dominant signal.

The image processing and overlay offset measurement device 130 may analyze an image relating to innate characteristics, e.g., critical dimension (CD) difference, an angle difference due to the overlay of circuit patterns, and exposure area, of the circuit patterns included in the structures LP1 and UP1 or LP2 and UP2 which are compared with each other and may measure the overlay offset OLO based on the results of the analysis.

FIGS. 5A through 5D are schematic diagrams including images generated based on electrons output from a sample and an overlay offset. ΔOVL indicates an offset between the center of a hole and the center of a line (or a line pattern).

Figure 5A:
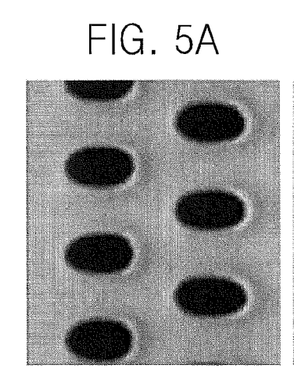
FIGS. 5A through 5D are schematic diagrams including images generated based on electrons output from a sample and an overlay offset.
Figure 5B:
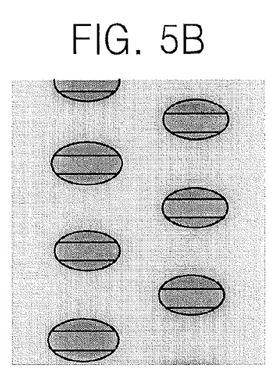

FIG. 5B shows an image of an active region, e.g., an edge of a metal contact, which is obtained using a SEM system having a high-energy electron source at a step of forming the metal contact for flash memory. At this time, the landing energy is 10 kV.

FIG. 5A shows an image of an active region, e.g., an edge of a metal contact, obtained based on SE detected using a CD-SEM system at a step of forming the metal contact for flash memory. At this time, the landing energy is 1 kV.

The clarity of the edge of the metal contact in the image illustrated in FIG. 5A is lower than that in the image illustrated in FIG. 5B. While the edge of the metal contact is not identified in the image illustrated in FIG. 5A, the edge of the metal contact is identified in the image illustrated in FIG. 5B.

Figure 5C:
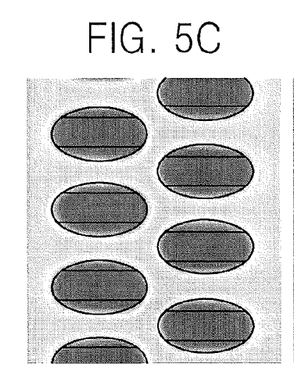

FIG. 5C shows an image of an active region which is obtained based on SE detected using a SEM system having a high-energy electron source at a step of forming a metal contact for flash memory. At this time, the landing energy is 15 kV.

Figure 5D:
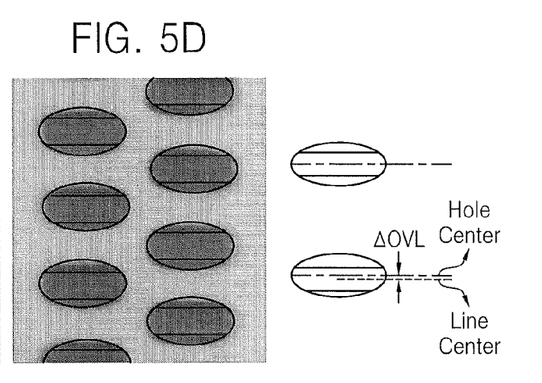

FIG. 5D shows an image of an active region, e.g., an edge of a metal contact, which is obtained based on BSE using a SEM system having a high-energy electron source at a step of forming the metal contact for flash memory. At this time, the landing energy is 15 kV.

When the image illustrated in FIG. 5C is compared with the image illustrated in FIG. 5D, the active region appears clearer in the image illustrated in FIG. 5D than in the image illustrated in FIG. 5C.

Figure 6A:
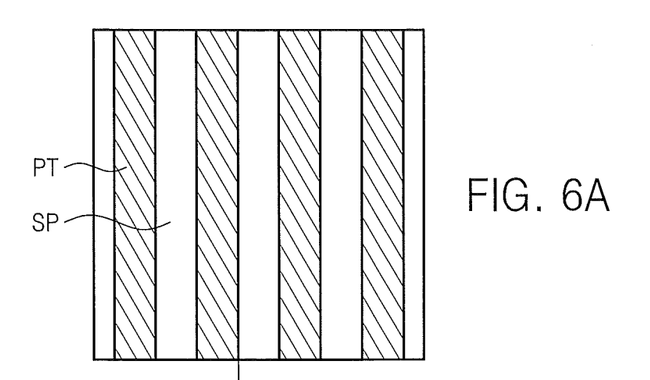
Figure 6B:
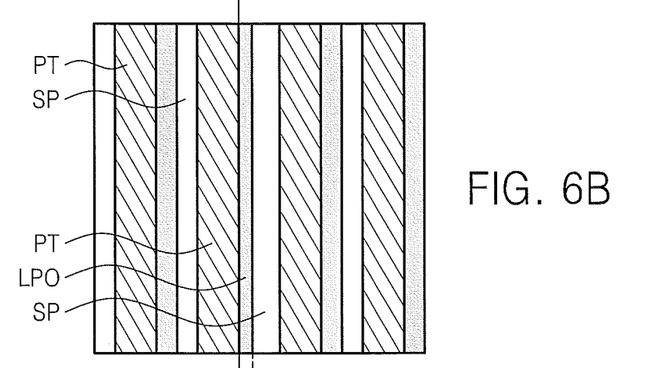
Figure 6C:
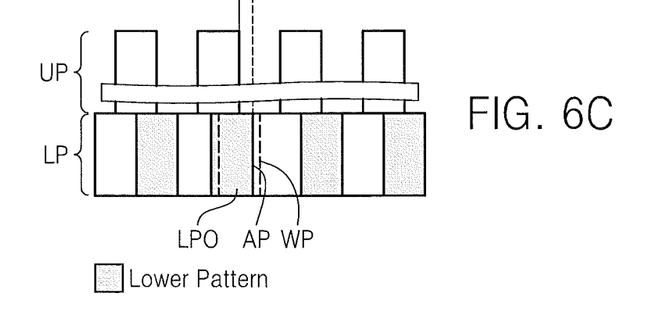
Figure 7A:
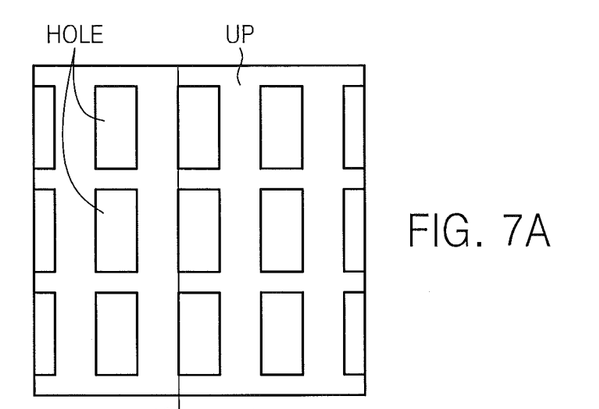
Figure 7B:
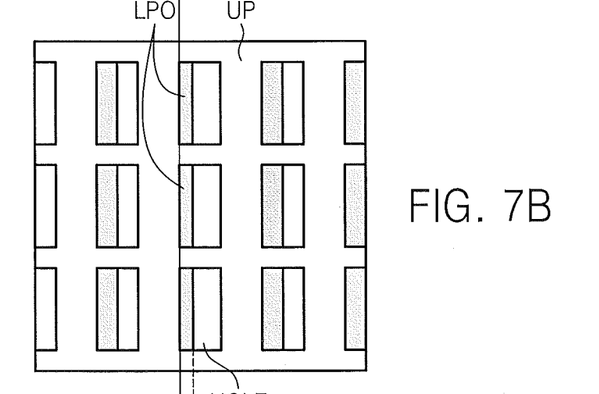
Figure 7C:
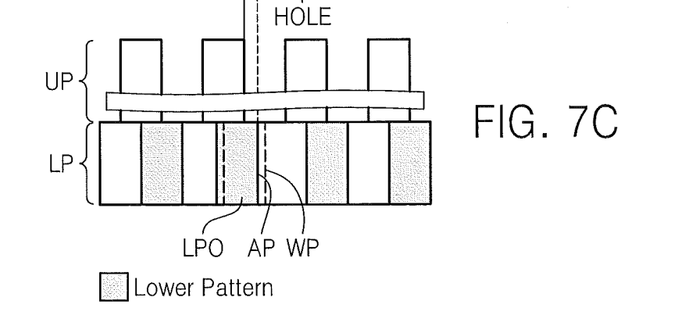
Figure 8A:
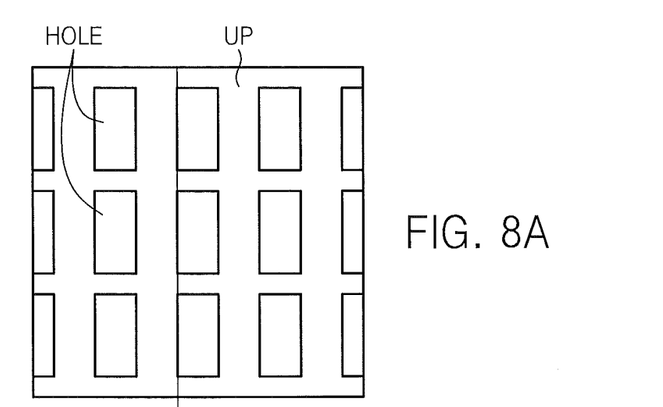
Figure 8B:
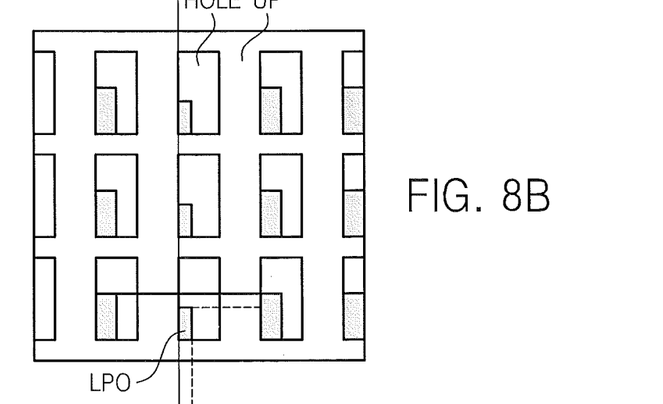
Figure 8C:
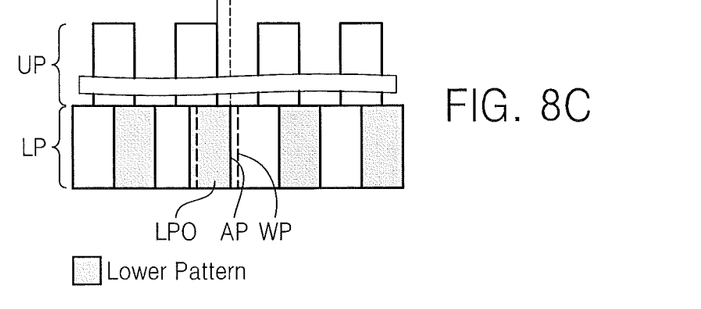

FIGS. 6A through 8C are schematic diagrams representing images measured using a conventional SEM system and images measured using a high-energy SEM system. Referring to FIGS. 6C, 7C, and 8C, the sample includes a lower structure LP formed at a child step in a multi-step process and an upper structure UP formed at a mother step in the multi-step process. The structures LP and UP include circuit patterns.

FIG. 6A shows a representation of an image including lines PT and spaces SP, which is obtained using the conventional SEM system. FIG. 6B shows a representation of an image including lines PT and spaces SP, which is obtained using the SEM system 100A or 100B (hereinafter, collectively denoted by 100) having a high-energy electron source, i.e., configured to provide an electron beam with a landing energy of at least 10 kV.

While an overlay offset cannot be measured from the image illustrated in FIG. 6A, an overlay offset of each pattern formed in the lower structure LP can be measured from the image illustrated in FIG. 6B. For instance, with reference to FIG. 6B, the image includes an image of a particular pattern LPO in the lower structure LP.

FIGS. 7A and 7B are schematic diagrams of a one-dimensional overlay of a two-dimensional array pattern. FIG. 7A shows a representation of an image including holes and upper patterns UP, which is obtained using the conventional SEM system. FIG. 7B shows a representation of an image including holes and upper patterns UP, which is obtained using the SEM system 100 having a high-energy electron source, i.e., configured to provide an electron beam with a landing energy of at least 10 kV.

While an overlay offset cannot be measured from the image illustrated in FIG. 7A, an overlay offset of each pattern formed in the lower structure LP can be measured from the image illustrated in FIG. 7B. For instance, with reference to FIG. 7B, the image includes an image of the particular pattern LPO in the lower structure LP.

FIGS. 8A and 8B are schematic diagrams of a two-dimensional overlay of a two-dimensional array pattern. FIG. 8A shows a representation of an image including holes and upper patterns UP, which is obtained using the conventional SEM system. FIG. 8B shows a representation of an image including holes and upper patterns UP, which is obtained using the SEM system 100 having a high-energy electron source, i.e., configured to provide an electron beam with a landing energy of at least 10 kV.

While an overlay offset cannot be measured from the image illustrated in FIG. 8A, an overlay offset of each pattern formed in the lower structure LP can be measured from the image illustrated in FIG. 8B. For instance, with reference to FIG. 8B, the image includes an image of the particular pattern LPO in the lower structure LP.

Figure 9:
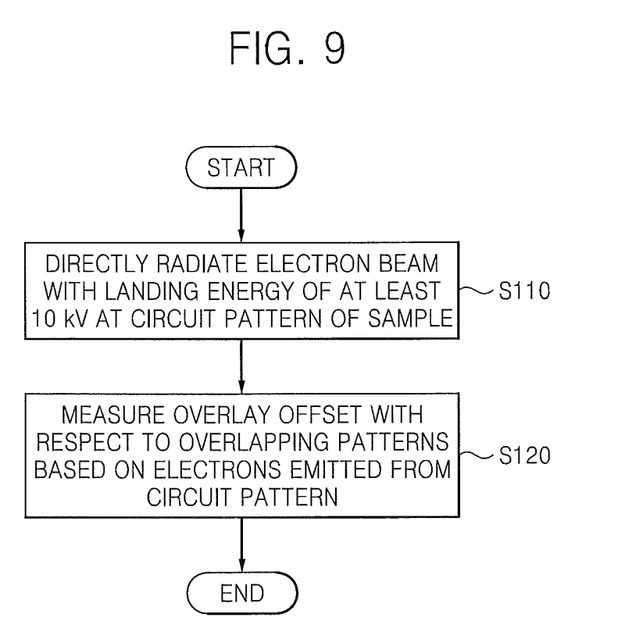
FIG. 9 is a flowchart of a method of measuring an overlay offset using the SEM systems illustrated in FIGS. 1 and 2.

FIG. 9 is a flowchart of a method of measuring an overlay offset using the SEM system 100 illustrated in FIGS. 1 and 2. Referring to FIGS. 1 through 9, a PEB with a landing energy of at least 10 kV is directly radiated at an in-cell region, e.g., a circuit pattern of the sample 117, in operation S110. The image processing and overlay offset measurement device 130 generates an image of overlapping patterns among patterns implemented in the circuit pattern using a signal related to or based on electrons emitted from the circuit pattern and measures an overlay offset with respect to the overlapping patterns using the image in operation S120. The method illustrated in FIG. 9 may be embodied as program code(s) programmed to a computer readable recording medium.

Embodiments of the present inventive concept can be embodied in hardware, software, firmware or combination thereof. When the method of measuring an overlay offset according to some embodiments of the present inventive concept is embodied in software, it can be embodied as computer readable codes or programs on a computer readable recording medium. The computer readable recording medium is any data storage device that can store data which can be thereafter read by a computer system. Examples of the computer readable recording medium may includes read-only memory (ROM), random-access memory (RAM), electrically erasable programmable ROM (EEPROM), and flash memory.

As described above, according to some embodiments of the inventive concept, a SEM system directly radiates an electron beam with a landing energy of at least 10 kV at a sample to measure an overlay offset with respect to overlapping patterns included in structures stacked in an in-cell region of the sample. The SEM system uses BSE emitted from the sample as dominant electrons, thereby accurately measuring the overlay offset.

While the inventive concept has been particularly shown and described with reference to exemplary embodiments thereof, it will be understood by those of ordinary skill in the art that various changes in forms and details may be made therein without departing from the spirit and scope of the inventive concept as defined by the following claims.

What is claimed is:

1. A method of measuring an overlay offset using a scanning electron microscope (SEM) system, the method comprising:

scanning once an in-cell region, which includes a lower structure and an upper structure stacked in a sample, by directly radiating a primary electron beam with a landing energy of at least 10 kV to the in-cell region, the in-cell region being a region in which actual circuit patterns are implemented, the upper structure stacked above the lower structure;

detecting electrons emitted from both the lower structure and the upper structure of the scanned in-cell region as a result of interaction, caused by the scanning once the in-cell region, between electrons included in the primary electron beam and the in-cell region; and measuring an overlay offset with respect to overlapping circuit patterns between a first actual circuit pattern included in the upper structure and a second actual circuit pattern included in the lower structure using images of the lower structure and the upper structure of the in-cell region that are simultaneously generated based on both the detected electrons emitted from the lower structure and detected electrons emitted from the upper structure of the scanned in-cell region, wherein, the sample is at an after clean inspection (ACI) step, the lower structure is formed at a first step in a multi-step process, the upper structure is formed at a second step in the multi-step process, the second step subsequent to the first step, and the second step is not performed right after the first step.

2. The method of claim 1, wherein the detected electrons are back-scattered electrons.

3. The method of claim 1, wherein the detected electrons are back-scattered electrons and secondary electrons.

4. The method of claim 3, wherein measuring the overlay offset comprises measuring the overlay offset using the images that are generated based on the back-scattered electrons in a greater degree than the secondary electrons.

5. The method of claim 1, wherein the in-cell region is separated from scribe lines of the sample and does not include alignment marks.

6. The method of claim 1, wherein the measuring step is carried out using an image processing and overlay offset measurement device.

7. The method of claim 1, further comprising displaying the measured overlay offset using a display.

8. A non-transitory computer readable medium storing a computer program configured to execute the method of claim 1.

9. A method of measuring an overlay offset using a scanning electron microscope (SEM) system, the method comprising:

scanning once an in-cell region of a sample by directly radiating a primary electron beam with a landing energy of at least 10 kV, wherein the in-cell region is a region in which actual circuit pattern are implemented and comprises a lower structure and an upper structure stacked in the sample, the upper structure stacked above the lower structure;

detecting back-scattered electrons emitted from both the lower structure and the upper structure of the scanned in-cell region as a result of interaction, caused by the scanning once the in-cell region, between electrons included in the primary electron beam and the in-cell region;

simultaneously generating images of the lower structure and the upper structure of the in-cell region that are based on the detected back-scattered electrons; and measuring an overlay offset with respect to overlapping circuit patterns between a first actual circuit pattern included in the upper structure and a second actual circuit pattern included in the lower structure using the generated images, wherein the sample is at an after clean inspection (ACI) step, wherein the lower structure is formed at a first step in a multi-step process, wherein the upper structure is formed at a second step in the multi-step process, the second step subsequent to the first step, wherein the second step is not performed right after the first step.

10. The method of claim 9, further comprising detecting secondary electrons emitted from the scanned in-cell region, wherein generating the images of the in-cell region comprises generating the images of the in-cell region that are based on the detected back-scattered electrons and the detected secondary electrons.

11. The method of claim 10, wherein the images are based on the back-scattered electrons to a greater degree than the secondary electrons.

12. The method of claim 9, further comprising displaying at least one of the generated images and the measured overlay offset.

13. The method of claim 9, wherein the detecting step is carried out using at least one detector that is positioned so as to not affect a path of the primary electron beam to the sample.

* * * * *